(12) United States Patent
Horber

(10) Patent No.: US 6,818,019 B2
(45) Date of Patent: Nov. 16, 2004

(54) JOINT PROSTHESIS

(76) Inventor: Willi Horber, Turbinenstrasse 12, CH-8005 Zürich (CH)

( * ) Notice: Subject to any disclaimer, the term of this patent is extended or adjusted under 35 U.S.C. 154(b) by 0 days.

(21) Appl. No.: 10/438,817

(22) Filed: May 16, 2003

(65) Prior Publication Data
US 2004/0030400 A1 Feb. 12, 2004

Related U.S. Application Data

(63) Continuation of application No. PCT/CH01/00674, filed on Nov. 16, 2001.

(30) Foreign Application Priority Data

Nov. 16, 2000 (CH) .............................................. 2235/00

(51) Int. Cl.$^7$ .............................. A61F 2/30; A61F 2/40; F16C 11/06
(52) U.S. Cl. ..................... 623/18.11; 403/90; 623/19.12
(58) Field of Search ............................ 623/18.11, 19.1, 623/1, 21.13, 22.11, 23.4, 48; 403/84, 90, 83; 606/53, 59

(56) References Cited

U.S. PATENT DOCUMENTS

| | | | | |
|---|---|---|---|---|
| 3,815,157 A | * | 6/1974 | Skorecki et al. ......... | 623/19.12 |
| 3,916,451 A | * | 11/1975 | Buechel et al. ............ | 623/23.4 |
| 3,978,528 A | * | 9/1976 | Crep ........................ | 623/19.12 |
| 4,011,603 A | | 3/1977 | Steffee | |
| 4,318,190 A | | 3/1982 | Cortesi | |
| 4,528,702 A | | 7/1985 | Frey | |
| 5,314,485 A | | 5/1994 | Judet | |
| 5,458,649 A | | 10/1995 | Spotorno et al. | |
| 5,522,903 A | | 6/1996 | Sokolow et al. | |
| 5,702,457 A | | 12/1997 | Walch et al. | |
| 5,702,471 A | | 12/1997 | Grundei et al. | |
| 5,741,335 A | | 4/1998 | Gerber et al. | |
| 5,888,207 A | | 3/1999 | Nieder et al. | |
| 6,093,208 A | | 7/2000 | Tian | |
| 6,102,951 A | | 8/2000 | Sutter et al. | |
| 6,132,467 A | * | 10/2000 | Keller ..................... | 623/18.11 |
| 6,197,063 B1 | | 3/2001 | Dews | |
| 6,228,120 B1 | | 5/2001 | Leonard et al. | |

FOREIGN PATENT DOCUMENTS

| | | |
|---|---|---|
| DE | 195 09 037 C1 | 9/1996 |
| DE | 195 09 037 C1 | 9/1996 |
| DE | 19548154 | 6/1997 |
| DE | 196 16 059 A1 | 10/1997 |
| DE | 29918589 | 3/2000 |

(List continued on next page.)

OTHER PUBLICATIONS

Search Report for PCT/CH00/00515 dated Jan. 30, 2001 (cited in SN 10/088,630.

(List continued on next page.)

Primary Examiner—David J. Isabella
(74) Attorney, Agent, or Firm—Burns, Doane, Swecker & Mathis, L.L.P.

(57) ABSTRACT

In a joint prosthesis the head cap is connected via a collar piece to the shaft piece which may be anchored in the bone. The collar piece is coupled to the shaft piece by a joint head in a ball-jointed manner. The articulation surfaces between the joint cavity in the shaft piece and the articulation head on the collar piece are embodied such that on pressing the articulation head to the base of the joint cavity, edges or projections on the one articulation surface digs into the other articulation surface lying on a virtual spherical surface. It is thus possible to achieve a ball-joint like articulation, whereby the spherical surfaces may have a relatively large production tolerance without the above affecting the clamping connection between the articulation surfaces.

23 Claims, 7 Drawing Sheets

FOREIGN PATENT DOCUMENTS

| | | |
|---|---|---|
| EP | 0 024 442 A1 | 8/1979 |
| EP | 0 208 578 A1 | 6/1986 |
| EP | 0 351 545 A1 | 6/1989 |
| EP | 0 532 440 A1 | 3/1993 |
| EP | 0 663 193 A1 | 12/1993 |
| EP | 0 586 335 A1 | 3/1994 |
| EP | 0 669 117 A1 | 8/1995 |
| EP | 0 679 375 | 11/1995 |
| EP | 0 712 617 A1 | 11/1995 |
| EP | 0 884 032 A1 | 6/1997 |
| EP | 0 805 609 | 12/1997 |
| EP | 0 903 128 | 3/1999 |
| EP | 0 963 741 A2 | 5/1999 |
| FR | 2 321 871 | 8/1975 |
| FR | 2 773 469 | 7/1999 |
| WO | WO 98/46172 | 10/1998 |
| WO | WO 99/34756 | 7/1999 |
| WO | WO 00/01327 | 1/2000 |
| WO | WO01/22905 | 9/2000 |

OTHER PUBLICATIONS

Search Reports for PCT/CH01/00676 dated Mar. 11, 2002 and Apr. 16, 2002.

Search Reports for PCT/CH01/00674 dated Feb. 26, 2002 and Jan. 16, 2003.

Search Report for PCT/CH01/00675 dated Feb. 26, 2002.

\* cited by examiner

JOINT PROSTHESIS

CROSS REFERENCE TO RELATED APPLICATIONS

This application claims priority under 35 U.S.C. §119 to Swiss Application 2235/00 filed in Switzerland on Nov. 16, 2000, and as a continuation application under 35 U.S.C. §120 to PCT/CH01/00674 filed as an International Application on 16 Nov. 2001 designating the U.S., the entire contents of which are hereby incorporated by reference in their entireties.

This application is also related to U.S. patent application entitled "Endoprosthesis For A Shoulder Joint", Ser. No. 10/088,630, filed Mar. 20, 2002, to U.S. patent application entitled "An Endoprosthesis For A Shoulder Joint", Ser. No. 10/438,836, filed on even date herewith and to U.S. Patent Application entitled "Joint Prosthesis", Ser. No. 10/438,970, filed on even date herewith, each of which is hereby incorporated herein by reference in its entirety.

BACKGROUND

1. Field

The invention relates to a joint prosthesis.

2. Background Information

A composite endoprosthesis with a metal shaft and a ceramic joint part is known from EP 0 024 442. The ceramic part has a conical or cylindrical recess. Support ribs are formed on a metal pin of the metal shaft, said pin being intended for introduction into the recess. Said ribs are plastically and elastically deformed on the fitting of the harder ceramic joint part. A press fit is thus obtained between the endoprosthesis parts.

From EP-A-0 712 617 a humeral head prosthesis is known wherein an articulation ball connected to a head cap via a shank is articulated on a shaft piece in a cavity with a hollow spherical base. To fix the articulation ball in the cavity, one or more grub screws are provided which can be screwed through the shaft piece against the articulation ball. In one exemplified embodiment, the articulation ball, which is of cut-open C-shape, is pressed together by the grub screw in order to clamp therein the shank which fits in a central bore in the articulation ball. In another exemplified embodiment, a grub screw is provided which can be screwed along the shank axis through the articulation ball and against the cavity base. With this screw the articulation ball is pressed against the opening of the cavity through which the shank projects from the cavity. In another example, projections cooperating with recesses in the ball surface are provided at the base of the cavity for indexing the position of the articulation ball in the cavity.

From WO 99/34756, which corresponds to FR-A-2 773 469, a shoulder prosthesis is known wherein a collar piece pivotable after the style of a ball joint in the shaft piece is articulated in a hemispherical recess in the shaft piece. The collar piece has a hemispherical articulation surface and a conical surface which is eccentric in relation to an axis through the ball center of said articulation surface, for the fitting of a joint cap thereon. The collar piece has a bore which is open from the cap side and has a hemispherical base. A screw with a spherical head which is introduced into the bore and which can be screwed into the shaft piece through an opening in the base of the bore is introduced into said bore. The spherical surfaces of the hemispherical recess in the shaft piece, the articulation surface on the shaft piece, the base of the bore and the screwhead must have the same center. Each two co-operating hollow and solid spherical surfaces must also be made very exactly and have the same radius. Minimal deviations from the ideal dimensions result in the collar piece being inadequately tightly connected to the shaft piece in order to reliably prevent unintentional pivoting of the collar piece relatively to the shaft piece during the use of the joint. The precision of the spherical surfaces required for the purpose has proved very difficult to achieve.

DE-U-299 18 589 has the object of precisely obviating this disadvantage of co-operating spherical surfaces. For this purpose it proposes an endoprosthesis for a shoulder wherein a rotary member is disposed in a shaft piece and is rotatable only about a first axis. A directional piece is articulated on the rotary piece for pivotal movement about just one second axis. A head cap can be disposed on the directional piece. The directional piece extends along a collar axis which—thanks to the first and second axes crossing one another—can be brought like a ball joint into any desired position and secured therein.

DE-U-299 18 589 teaches avoiding the ball joint and simulating the ball joint movement by dividing it into two independent movements about two discrete axes. The articulation and friction surfaces between the shaft piece, rotary member and directional member, due to the fact that spherical surfaces were avoided, are surfaces of bodies of rotation such as a cylinder, torus and cone. These surfaces are much simpler to make with sufficient precision.

To secure the pivoting movement of the directional member relatively to the rotary member, it is proposed that the co-operating articulation surfaces should advantageously simply so correspond that linear contact takes place between them. For this purpose, the articulation surface on the rotary member can be constructed as a channel with two planar surfaces at an angle to one another. A bore in the directional member against which the spherical head of a screw presses, can also be made conical. It is further proposed that the articulation surfaces can also have edges and pins which are adapted to be pressed into the co-acting surface during the tightening of the screw. No example of this is given.

SUMMARY

The present invention is directed to a joint prosthesis with a shaft piece for anchoring in the bone and a collar piece articulated thereon in the manner of a ball joint, and a head cap disposed on the collar piece, both to increase the production tolerances for the articulation surfaces involved in the ball joint and also increase the reliability of immobilizing the ball joint compared with the prior art.

According to the invention, in an exemplary joint prosthesis, at least one first one of the two co-operating articulation surfaces has at least one edge and/or point. In addition, the articulation surfaces are so constructed in respect of their shape that only one or more contact zones occur between the edge and/or point of the first articulation surface and the second articulation surface lying on a virtual spherical surface. In addition, the articulation surfaces are so constructed with respect to material that under the action of the pressure forces occurring during the pressure application at least the second articulation surface is plastically deformable in the contact zone by the edge and/or point of the first articulation surface.

As a result, when the pressure piece is pressed into contact, at least one edge or point of one articulation surface digs into the second articulation surface thus providing engagement of the two articulation surfaces by a toothing or clawing effect. The toothing allows the production tolerances to be raised. As a result, even if the surface shapes do not correspond, and even in the event of relatively considerable inaccuracies of dimensions, a ball joint is created which can be reliably immobilized. To pivot or turn the joint head relatively to the joint cavity once the head has been fixed, requires deformation of the material and therefore very considerable forces. Nevertheless, the joint head is guided in the joint cavity and pivotable in the manner of a ball joint as long as the pressure piece is not pressed tightly into contact but simply bears in contact.

The joint prosthesis has a shaft piece for anchoring in the bone. This is adapted to the bone in known manner and is optionally selected from a set of shaft pieces. A collar piece is articulated on the shaft piece and defines a collar axis. The collar piece is equipped to receive a head cap or part of the head cap. The joint prosthesis is also provided with a head cap which is designed for the joint socket co-operating with the head cap. The head cap is as far as possible shaped so as to approximate the distal natural cap and is optionally therefore selected also from a set of caps. The joint prosthesis also comprises at least one pressure piece for pressing the collar piece against the shaft piece and means for connecting the pressure piece and the shaft piece. For the articulation of the collar piece on the shaft piece there is formed either on the collar piece or on the shaft piece a joint cavity and on the other piece a joint head for disposing in the joint cavity. The joint head is pivotable or turnable in the joint cavity at least about two axes at right angles to one another. Depending on whether the joint socket is or is not also replaced, the joint prosthesis also has an artificial joint socket anchorable in the bone. If the natural socket is retained, the head cap co-operates therewith.

The plastic deformation of a contact zone in the joint cavity or a contact zone on the articulation surface of the joint head not only has the result that the necessary precision of the parts can lie within conventional production tolerances and no increased requirements apply to the production and checking of dimensional stability of the parts. The deformation of the articulation surface also results in a non-pivotable connection between the shaft piece and the collar piece. In the deformed zone, if the articulation surfaces are pressed, both or else just one participating surface can be deformed. If it is predominantly the collar piece which experiences deformation, this can be replaced, for example on a revision of the joint prosthesis, without it being necessary to replace the shaft piece.

If the contact zones between the base of the joint cavity and the joint head have one or more punctiform contacts, or even one or more continuous or interrupted linear contacts, the magnitude of the pressure exerted in these zones is inversely proportional to the size of the contact zones. In this way more intensive deformations can be obtained.

If one of the articulation surfaces is formed by one or more body edges or one or more body points and the other articulation surface is formed by a surface zone, the body points and body edges are pressed into the other articulation surface and deformed articulation surfaces form, the alignment of which is situated transversely of a tangent to a circle about the pivot center. This results in a toothing between the collar piece and the shaft piece, and therefore a secure connection which also withstands relatively considerable forces on the ball joint between the base and the collar piece. The surface zone can be smooth or rough. The possibilities of the meaning of smooth extend from untreated after machining, to polished. A rough surface can be grooved or porous, it can be etched, blasted, cast or machined or otherwise structured. Advantageously, it should be considered that the two articulation surfaces remain pivotable practically continuously relatively to one another. Rough surfaces are therefore more suitable for linear contact and smooth surfaces more for point contact.

In the exemplified embodiments, the contact zone is situated on a virtual spherical surface. An advantage of this is that the pivotability after the style of a ball joint between the collar piece and the shaft piece is obtained without additional steps. If one articulation surface, for example of the joint head, is a spherical surface, an articulation surface cooperating with this spherical surface zone advantageously forms edges situated transversely of the strongest torques acting on the collar piece before and after clamping. This prevents turning of the collar piece about the collar axis, thus ensuring that the selected position between the collar piece and the shaft piece is not changed during or after the compression of these two parts. Conversely, the spherical surface zone may have grooves and edges. These are also advantageously situated transversely of the strongest torque acting on the collar piece.

In addition to the small contact area zones between the shaft piece and the collar piece, it is also advantageous to provide such zones between the collar piece and the pressure piece. There is therefore advantageously at least one continuous or interrupted linear contact between the joint head and the pressure piece.

BRIEF DESCRIPTION OF THE DRAWINGS

The invention will now be explained with reference to exemplified embodiments. In the drawings.

DETAILED DESCRIPTION OF THE DRAWINGS

Figure 1:
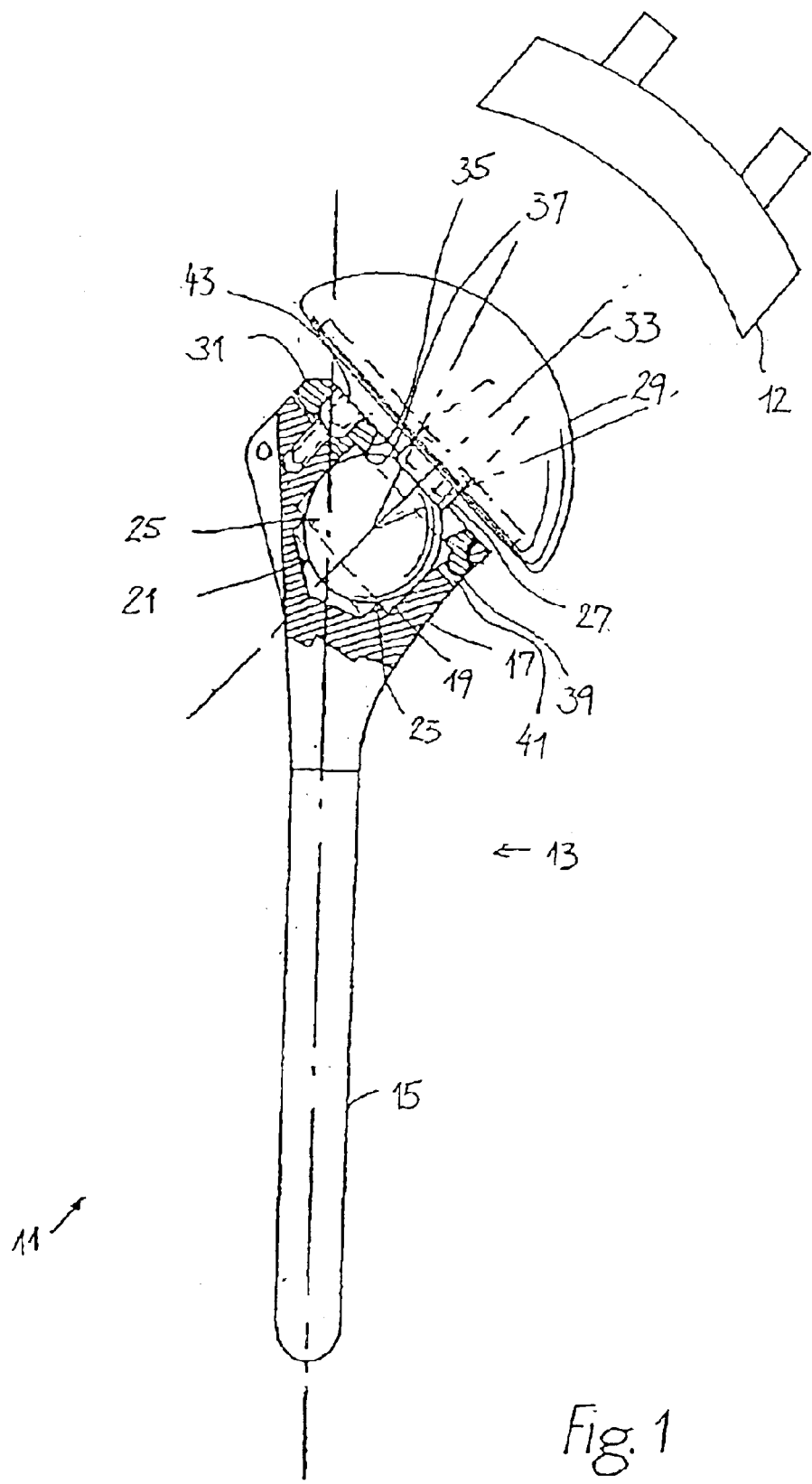
FIG. 1 is a partial section through a shoulder joint prosthesis according to an exemplary embodiment of the invention with a spherical joint head in a joint cavity with a circular edge as articulation surface.

For the sake of clarity, like and similar parts have the same reference numerals in the following detailed description of the exemplified embodiments.

The shoulder joint prostheses 11 illustrated in FIGS. 1 to 9 and 13 comprise a shaft piece adapted to be anchored in the patient's humerus bone or a shaft piece 13 with a shaft shank 15 and a shaft head 17. A joint cavity 19 is formed in the shaft head 17. A collar piece 21 is articulated on the shaft piece 13. It comprises an articulation head 25 bearing in the joint cavity 19 and a collar extension 27. A head cap 29 is fitted or adapted to be fitted on the collar extension 27 and co-operates with an artificial glenoid 12, as shown in FIG. 1, or with a natural glenoid.

A collar axis 33 is defined by the direction of the collar extension 27. In a middle position of the collar piece 21, the collar axis 33 coincides with the axis of the joint cavity 19. This direction of the collar axis 31 must be adjusted individually for each patient. To enable the collar axis 33 to be aligned in respect of inclination and anteversion or retroversion, for example perpendicularly to the sectional surface at the patient's bone, the collar piece 21 is mounted in the joint cavity 19 after the style of a ball joint. The collar axis is thus adapted to be deflected from the middle position through an angle of about 20° in any direction.

FIG. 1 shows a first exemplified embodiment of a shoulder joint prosthesis in which a circular edge 23 at the base of the joint cavity 19 forms a bearing for the ball of the joint head 25. Said circular edge 23 is formed by the orifice edge of a central second bore in the flat base of a first bore in the shaft head 17, said first bore forming the main volume of the joint cavity 19. The larger first bore has a radius corresponding to the ball radius of the joint head 21, but may also be larger to enable the joint head 25 to be inserted into the joint cavity 19. The smaller second bore has a radius corresponding approximately to the circular edge 23. The joint ball 25 is guided by the two circular edges 23, 37 of the smaller bore and of the passage opening 35.

A passage opening 35 for the collar extension 27 is formed in the pressure application disc 31. Its diameter can correspond to that of the second bore. The passage opening 35 has a circular opening edge 37, which bears against the joint head 25. On one side, the pressure disc 31 is articulated by a hinge nose 39 in a hinge recess 41 in the shaft head 17. The hinge nose 39 and hinge recess 41 are adapted to be pushed into one another so that the pressure disc 31 and the shaft piece 13 can be released from one another. On the hinge side, a slot can be formed in the pressure disc 31 between two hinge noses 39 so that the pressure disc 31 is horseshoe or C shaped. On the side opposite the hinge nose the pressure disc 31 is screwed to the shaft head 17 by a screw 43. This gives a three-point clamping between the two hinges 39, 41 and the screw 43.

If the circular edges 23 and 37 bear against the ball surface of the joint head 25 without pressure being exerted on the latter, the collar piece 21 is pivotable relatively to the shaft head 17 after the style of a ball joint. To fix the joint head 21 in the shaft head 17, the screw 43 is tightened so that the two circular edges 23, 37 are moved towards one another. In these conditions, the circular edges 23, 37 are pressed into the ball surface of the joint head and deform it plastically. This gives a very stiff connection between the collar piece 21 and the shaft piece 13 anchorable in the bone.

Figure 2:
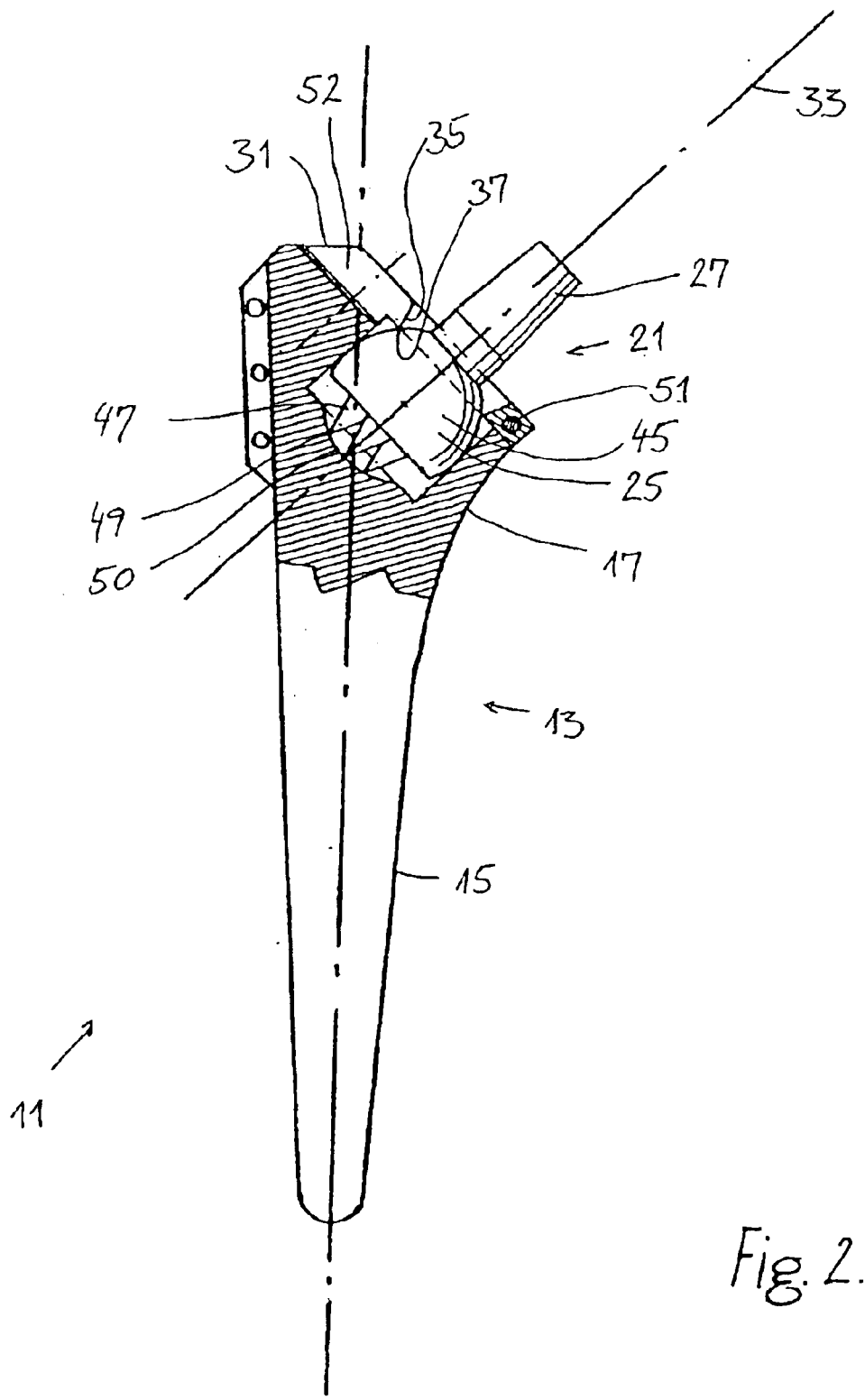
FIG. 2 is a partial sectioned view of an exemplary shoulder joint prosthesis without a head cap and with points on the joint head of the collar piece, said points being directed against a spherical base of the joint cavity.

FIG. 2 shows a second exemplified embodiment of a shoulder joint prosthesis 11. The joint head comprises a spherical surface zone 45 and three pointed members 47. The points 49 of the members 47 have the same distance from the ball center as the spherical surface. The points 49 are directed towards the base of the joint cavity 19. In the pivoting zone of the points 49 the joint cavity 19 has a hollow spherical surface 50 with the same radius as the spherical surface of the joint head 21. The points 49 bear against this hollow spherical surface. The hollow spherical surface 50 is formed in the base of a cylindrical joint cavity 19. A great circle of the spherical surface of the joint head 21 is in contact with the cylindrical generatrix of the joint cavity 19.

A collar extension 27 extends through a passage opening 35 in a pressure application disc 31. A head cap selected from a set of head caps is fixed on it. The pressure disc 31 is articulated on one side on the shaft head 17 by a pivot 51 and is pivotable with respect to the shaft head 17 about the pivot 51. The pressure disc 31 is C-shaped and the C-opening 52 points away from the pivot 51. Thus when the pressure disc 31 is swung up the joint head 25 can first be introduced into the joint cavity 19 and then the disc can be swung back. The pressure disc 31 is adapted to be screwed to the shaft head 17 by a screw in each of the two C-limbs (only the axis of the screw is shown). Here, as in the first exemplified embodiment, the passage opening 35 has an opening edge 37 directed towards the joint head 25 lying in the joint cavity 19. When the screw 43 is tightened, the joint head 25 is pressed with this opening edge 37 against the base of the joint cavity 19. In these conditions, the points 49 of the pointed members 47 dig into the hollow spherical surface 50 of the joint cavity 19. Depending on the pressure conditions and the materials selected, the opening edge 37 also digs into the spherical surface of the joint head.

Figure 3:
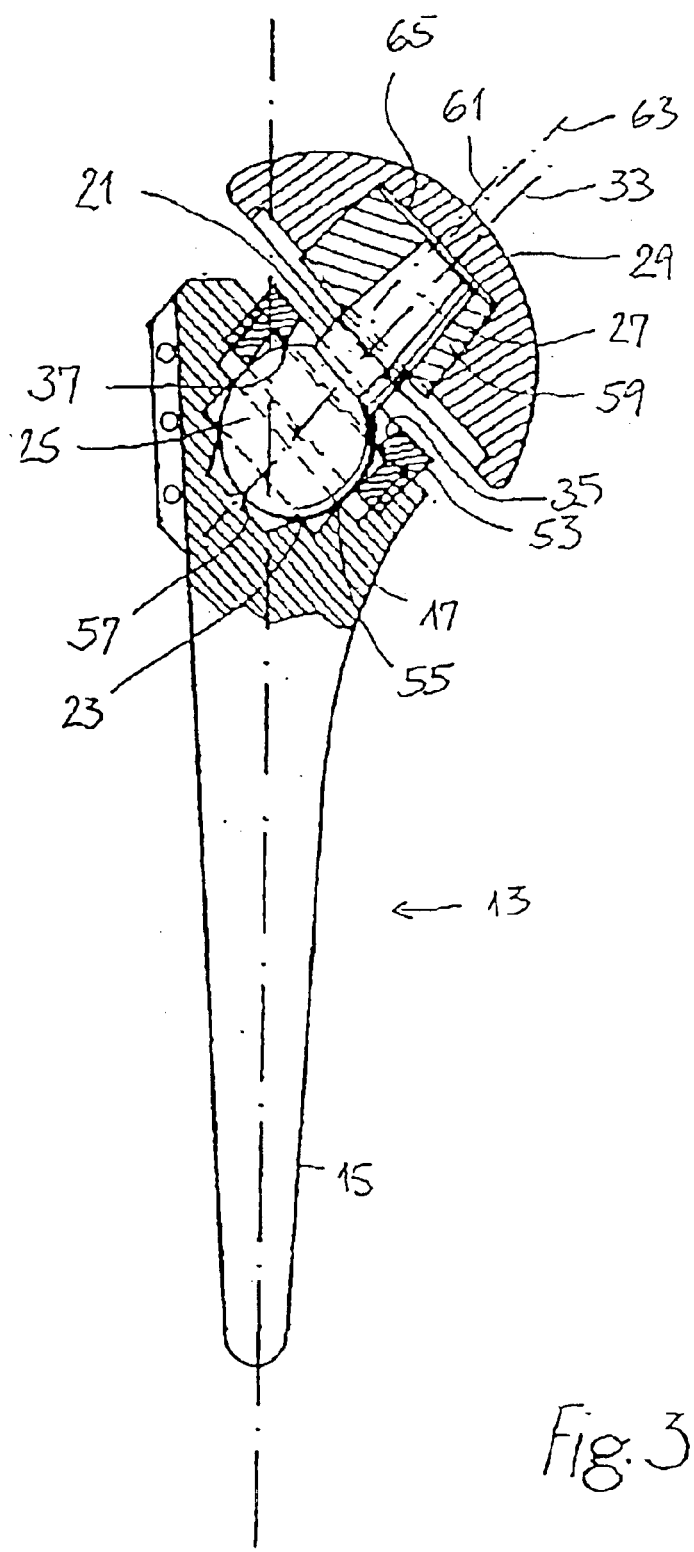
FIG. 3 is a partial section of an exemplary shoulder joint prosthesis with a spherical joint head and circular edges pressable into the joint head and also a point of this kind in the base of the joint cavity.

In the third exemplified embodiment shown in FIG. 3, the pressure piece is formed by a cap nut 53. This is adapted to be screwed into the joint cavity 19 in a screwthread in the edge of the latter. Like the cap nut in the exemplified embodiments shown in FIGS. 6 and 7, it can also surround the edge of the joint cavity 19. Here, however, the cap nut also bears against the spherical joint head 25 along practically a great circle and thus forms a lateral guide for said head. This guide is not absolutely necessary, since guidance of the joint head 25 is already provided by the two circular edges 23 and 37. Like the pressure plate 31 in the first two exemplified embodiments, the cap nut engages the joint head 25 with the opening edge 37 of the passage opening 35 for the collar extension 27.

The cylindrically stepped joint cavity 19 has a first radius with the screwthread. A smaller second radius has almost the radius of the joint head 25. The orifice edge of this second hollow cylinder with the second radius forms a first circular edge 55. During the pressing operation the joint head is pressed into this second hollow cylinder, a clamping fit occurring between the joint head 25 and the first circular edge 55. A second circular edge 23 with a smaller radius than the first and a point 57 on the axis 33 of the cylindrical bore at the base of the joint cavity 19 lies approximately on a spherical surface having the same radius as the ball of the joint head 25. When the joint head 25 is pressed into the joint cavity 19, they dig into the surface of the joint head.

FIG. 3 also shows a double eccentric for accurate alignment of the head cap 29 to the contour line of the sectional surface at the bone. The double eccentric is made up of an eccentric ring 59 which is adapted to be pushed on to the collar extension 27, having the axis 61, and a recess 65 disposed eccentrically to the cap axis 63 in the head cap 29 to receive the eccentric ring 59. A clamping fit is provided between the collar extension 29 and the eccentric ring 59, and between the latter and the recess 65. It is necessary to separate the collar piece 21 and the eccentric ring 59 because the eccentric ring 59 does not fit through the passage opening 37. If the collar extension 27 is insertable into the joint head 25, the eccentric ring 59 can also be made in one piece with the collar extension 57.

Since the invention is independent of the shape of the shaft piece or shaft piece 13, FIGS. 4 to 9 show only the shaft head 17 with the collar piece 21 and the pressure piece, partly with and partly without eccentric and head cap 29.

Figure 4:
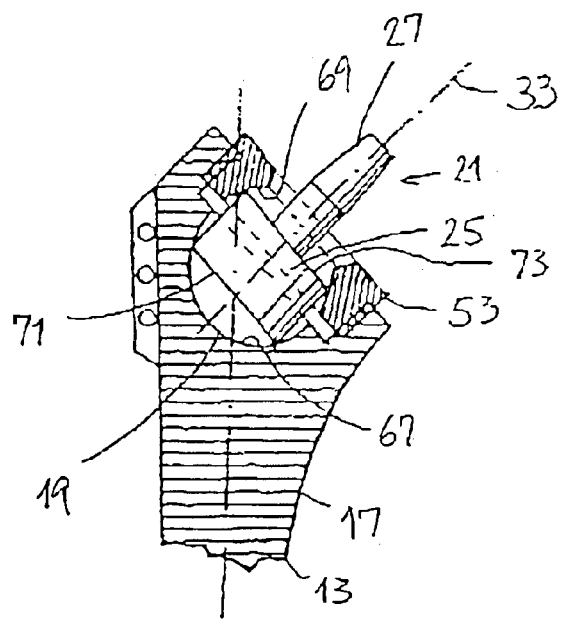
FIG. 4 is a partial section of the head zone of an exemplary shoulder joint prosthesis with a cylindrical joint head in a spherical joint cavity.

FIG. 4 shows a fourth exemplified embodiment with a joint cavity 19 in the shaft head 17 with a substantially hemispherical articulation surface 67, a cap nut 53 with a concave, substantially hemispherical articulation surface 69 and a collar piece 21 with a cylindrical joint head 25. The cylindrical joint head 25 has two circular edges 71, 73 one of which co-operates with the articulation surface 67 of the joint cavity 19 and the other with the articulation surface 69 of the cap nut 53. The circular edges 71, 73 are situated on a virtual spherical surface with substantially the same radius as the spherical surfaces 67, 69 of the joint cavity 19 and the cap screw 53. To adjust the radius of the virtual spherical surface all that is necessary is to change the length of the joint head 25. The radius of the virtual sphere is advantageously somewhat larger than the radius of the hollow spherical surfaces of the two articulation surfaces 67, 69. It is easy to obtain sufficient accuracy of the correspondence of the two sphere radii, since the articulation surfaces 67, 69 and the circular edges 71, 73 are plastically deformable.

Figure 5:
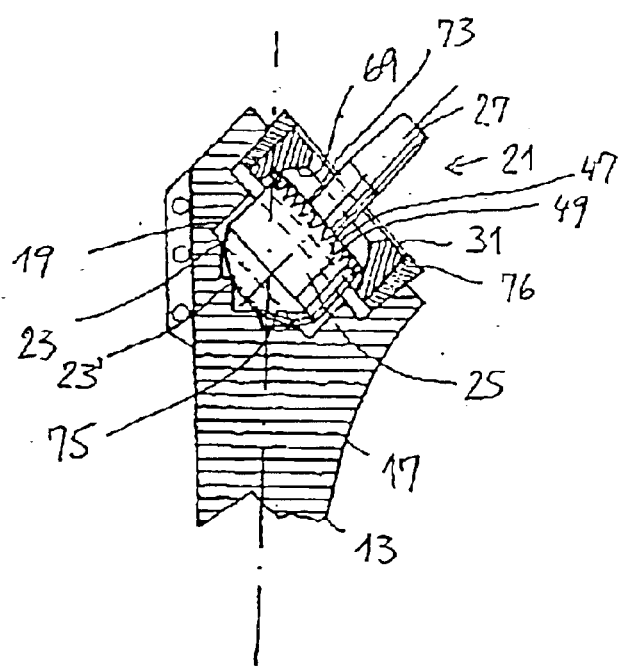
FIG. 5 is a partial section of the head zone of an exemplary shoulder joint prosthesis with circular edges formed at the base of the joint cavity and in contact with a spherical surface on the joint head and an interrupted circular line as an articulation surface between points situated on a circle, on the articulation head, and a spherical surface on the pressure piece.

FIG. 5 shows a fifth exemplified embodiment in which the pressure plate 31 is not a cap nut with a screwthread but holds in the shaft head 17 by a clamping fit. It has a hollow spherical articulation surface 69 which co-operates with an interrupted circular edge 73 on a partially cylindrical joint head 25. The circular edge 73 is divided up by incisions in the joint head 25 to form a series of body points 47, the points 49 of which dig into the articulation surface 69 when the pressure disc 31 is knocked into the shaft head 17. The joint cavity 19 has two circular edges 23, 23' which co-operate with a spherical surface 75 on the joint head 25. In this exemplified embodiment also, it is relatively easy to obtain correspondence of the radii of the spherical surface 75 and of the circular edge 73 at the joint head 25, with the radii of the virtual spherical surface on which the circular edges 23, 23' lie and of the articulation surface 69 at the pressure disc 31, since the required deformation of the contact zones allows larger tolerances than the pressing of two congruent articulation surfaces can. Clamping between the shaft piece 13 and the pressure disc 31 can be achieved directly by way of a cone. Preferably, however, the clamping of the pressure disc 31 is obtained as illustrated by means of a wedge clamping with, for example, a wedge 76 engaging in the form of a C round the pressure disc.

Figure 6:
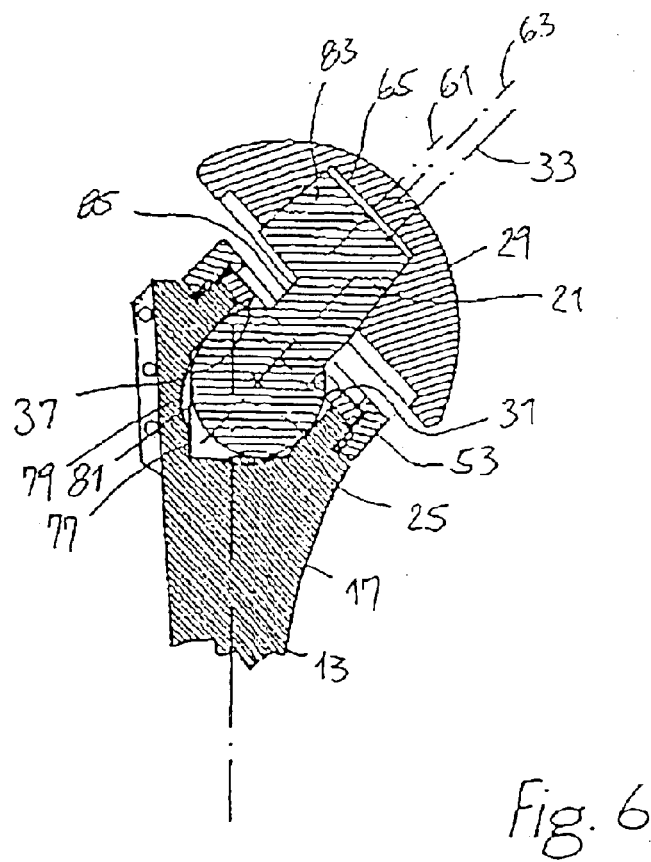
FIG. 6 is a sectional view through the head zone of an exemplary shoulder prosthesis with a spherical joint head and a conical base for the joint cavity.

The sixth exemplified embodiment shown in FIG. 6 comprises a conical base 77 for the joint cavity 19 and a spherical joint head 25 on the collar piece 21. The surface of the base 77 has incisions 79 in the direction of the generatrices through the cone apex. The result is the formation between the incisions 79 of edges 81 transversely of a direction of rotation about the axis 33. The pressure disc 31 is fixed on the shaft head 17 by a cap nut 53. The collar piece 21 is integrally equipped with an eccentric 83. The pressure disc 31 is C-shaped. The C-opening has a width which enables a collar zone 85 to be introduced between the joint head 25 and the eccentric member 83 of the collar piece 21 through said C-opening into the passage opening 37 of the pressure disc 31. The cap nut 53 is either also C-shaped or has an opening width which enables the cap nut 53 to be pushed down over the eccentric member 83 or up over the joint head 25 on to the collar piece 21. In the latter case, the cap nut first has to be pushed over the joint head 25 and then the pressure disc 31 has to be inserted between the joint head 25 and the cap nut 53. In this example, the articulation disc 31 is rotatable relatively to the cap nut 53. The advantage of this is that on tightening of the cap nut 53 a torque can be transmitted to the collar piece 21. On the tightening of the cap nut 53 the opening edge 37 is not turned relatively to the joint head 25 but only pressed against the latter. In the untightened state the collar piece 21 can be turned around the collar axis 33. As a result, the eccentric member 83 can be brought into the required position.

Figure 7:
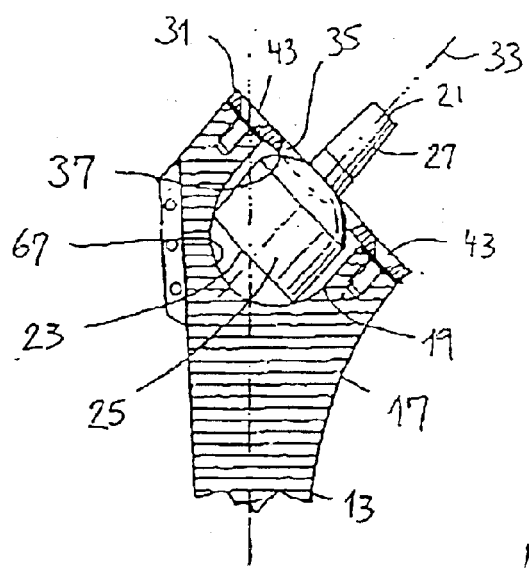
FIG. 7 is a partial section of the head zone of an exemplary shoulder prosthesis with a hemispherical base for the joint cavity and a joint head formed cylindrically therein towards said base and which comprises a spherical surface towards a pressure disc with a circular edge as articulation surface.

FIG. 7 shows by reference to a seventh exemplified embodiment a very simple variant of the pressure plate and another possibility of combining cylindrical and spherical members and openings to achieve a connection in the form of a ball joint which has already been constructed a number of times between the joint cavity and the joint head and between the shaft head 17 and the collar piece 21. In this example, the joint cavity has a hemispherical base 67 which co-operates with a circular edge 23 of a cylindrical joint head 25. Towards the pressure disc 31, however, the joint head is of spherical construction so that the circular opening edge 37 of the pressure disc 31 bears uniformly against the joint head in any pivoted position thereof. The articulation disc 31 is adapted to be screwed to the shaft head 17 by two screws 43.

Figure 8:
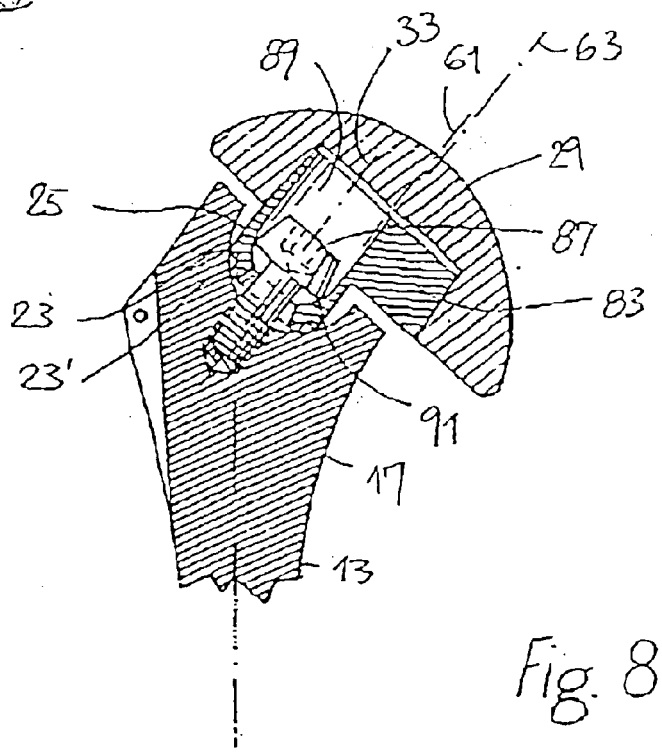
FIG. 8 is a section through the head zone of an exemplary shoulder prosthesis with a hemispherical joint cavity and a cylindrical joint head, wherein the pressure means is a screw through the center of the joint head.

FIG. 8 shows that the invention can also be applied without a pressure disc 31. In this eighth exemplified embodiment the collar piece 21 is of cylindrical construction and the joint head 25 is stepped to form two circuit edges 23, 23' on a virtual spherical surface. These circular edges 23, 23' co-operate with the hollow spherical surface of the joint cavity 19. The collar piece 21 is now of hollow construction and a screw 87 fits in this cavity 89 in such manner that its screwthreaded portion emerges through an end-face opening in the collar piece and is adapted to be screwed in the base of the joint cavity. A circular edge 91 is formed on the frusto-conical screw head and co-operates with a hollow spherical surface at the base of the cavity 89. The collar piece 21 is made integral with the eccentric 83. In the tightened state of the screw 87, the edges 91, 23, 23' are pressed into the spherical surfaces and thus reliably prevent any pivoting of the collar piece 21 relatively to the shaft head 17. The centers of the different spherical surfaces then advantageously practically coincide. Smaller deviations from an exact correspondence of the sphere centers are, however, compensated by the deformations.

The exemplified embodiments can also be modified to the effect that the joint cavity is formed in the collar piece and the joint head in the shaft head. The collar extension need not be made integral with the joint head but can be provided as a shank which can be secured in the joint head. The construction of the pressure piece is substantially independent of the construction of the articulation surfaces between the joint cavity and the joint head, so that the most diverse combinations are possible amongst the embodiment variations shown and mentioned.

Figure 9:
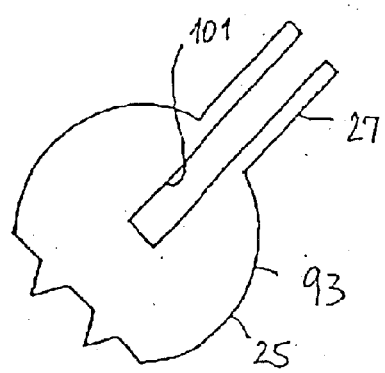
FIGS. 9 and 10 are views of two exemplary parts together forming a collar piece.
Figure 10:
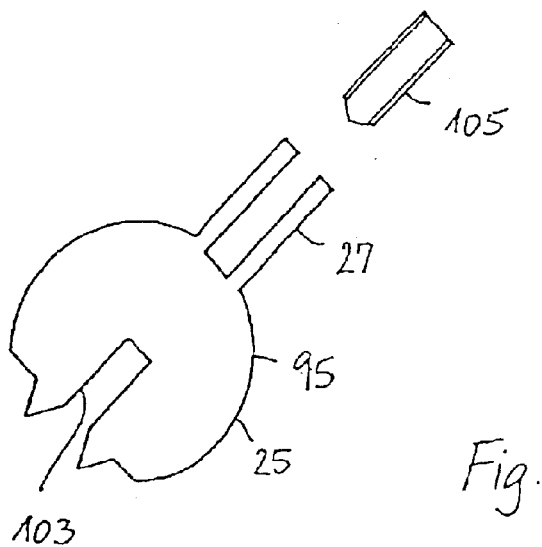
Figure 11:
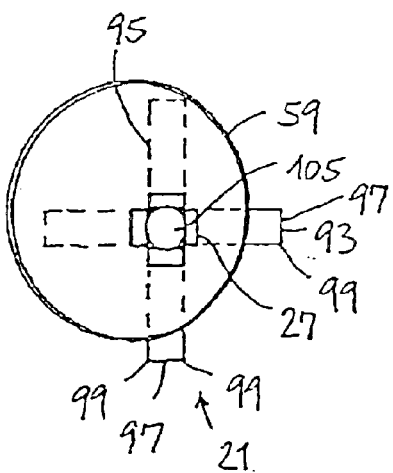
FIG. 11 is a plan view of the collar piece made up of the parts shown in FIGS. 9 and 10 with an eccentric ring.

It should also be noted that the joint head 25, for example, need not be a solid member. It can, for example, as shown in FIGS. 9 to 11, be made up of individual parts. FIGS. 9 and 10 show the elevations of two parts 93 and 94 in the form of plates which can be fitted together. Assembled the parts 93, 95 form a collar piece 21 which can be used instead of the collar piece 21 in FIG. 2. The parts 93, 95 are simple to make. For example they can be laser cut from a plate or be cast. The edge surface 97 need not be a spherical surface. As a result of pressing into the joint cavity the edges 99 are so deformed that there is a large-area contact and also very good toothing between the shaft head 17 and the collar piece 21. The part 93 in FIG. 9 can be pushed with the slot 101 across the slot 103 on the part 95 in FIG. 10 on to said part 95 so that all the edges 99 are situated on a common spherical surface. In the collar extension 27 there is formed in both parts 93, 95 a groove into which a screw 105 can be screwed.

The collar extension 27 made up of the two parts 93, 95 forms a cross with a central square recess. The eccentric ring 59 can be placed on this cross. As a result of the cross shape of the collar extension 27 and a corresponding recess in the eccentric ring, it is impossible for the eccentric ring 59 to turn relatively to the collar piece 21. To fix the eccentric ring 59 on the collar extension 27 and the two parts 93, 95 against one another, the screw 105 can now be screwed in, resulting in clamping between the parts 93, 95 on the one hand and the eccentric ring 59 on the other hand. In FIG. 11, the assembled collar piece 21 with the eccentric ring 59 is shown in plan view. This view shows how the edge surfaces 97 of the two parts are constructed orthogonally to the plate plane.

Figure 12:
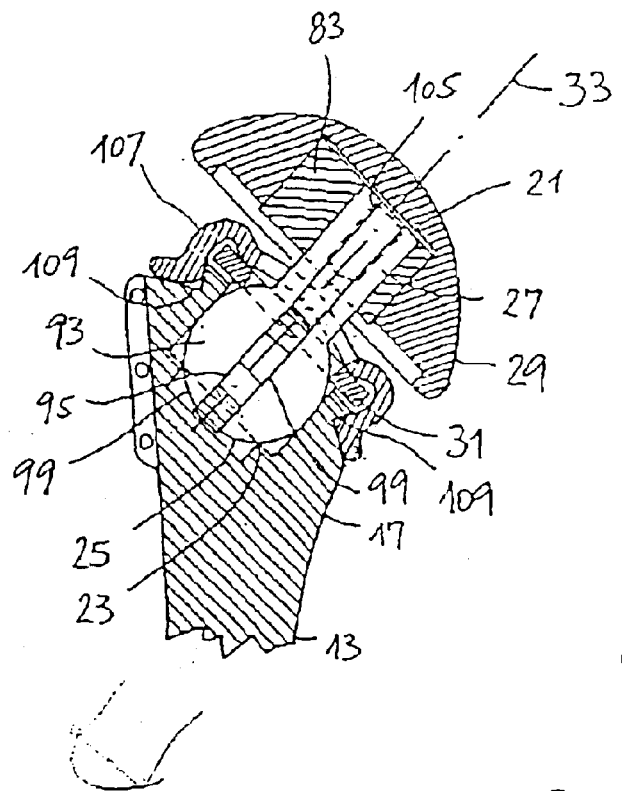
FIG. 12 is a partial section of an exemplary shoulder joint prosthesis with a collar piece according to FIGS. 9 to 11 and a clamping member.

FIG. 12 shows a tenth exemplified embodiment in which the collar piece 21 is made up of two parts 93, 95. Except for the shape of the joint head 25, the collar piece 21 corresponds exactly to the collar piece 21 shown in FIGS. 9 to 11. The shaft head 17 is provided with a cylindrical joint cavity 19 in which a body edge 23 is formed against which the edges 99 of the collar piece 21 bear. The collar piece 21 is pressed by a pressure disc 31 against the base of the joint cavity 19. The force with which the pressure disc 31 is pressed against the shaft 13 is transmitted by a clamping member 107 on to the said disc 31. The clamping member 107 bears against the outside of the pressure disc 31 and engages behind an undercut 109 in the shaft head 17. It is made from a resilient material so that a relatively large force is exerted on the pressure plate. The clamping member 107 can also directly form the pressure disc 31.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A joint prosthesis, comprising:
   an artificial joint socket for anchoring in a first bone, or for an articulating co-operation with a natural joint socket in a first bone;
   a shaft piece for anchoring in a second bone;
   a joint cavity in the shaft piece;
   a collar piece which defines a collar axis and comprises a joint head, which joint head is disposed in the joint cavity;
   articulation surfaces co-operating in the joint cavity and at the joint head such that the collar piece is articulated on the shaft piece as a ball joint;
   at least one pressure piece for pressing the joint head into the joint cavity;
   means for connecting the pressure piece and the shaft piece; and
   a head cap disposed on the collar piece, wherein at least a first one of the co-operating articulation surfaces has at least one edge and/or point and a second articulation surface lies on a virtual spherical surface such that at least one punctiform and/or linear contact zone is present between the first articulation surface and the second articulation surface, and wherein the articulation surfaces are constructed of material such that under pressure force during pressing into contact at least the second articulation surface is plastically deformable by the edge and/or point of the first articulation surface.

2. A joint prosthesis according to claim 1, wherein the second articulation surface is formed by a surface zone.

3. A joint prosthesis according to claim 1, wherein the edge is situated transversely of a direction of rotation of the collar piece about its collar axis.

4. A joint prosthesis according to claim 1, wherein the surface zone is spherical and has grooves.

5. A joint prosthesis according to claim 4, wherein the grooves are situated transversely of a direction of rotation of the collar piece about its collar axis.

6. A joint prosthesis according to claim 1, wherein at least one linear contact exists between the joint head and the pressure piece.

7. A joint prosthesis according to claim 1, wherein the pressure piece and the shaft piece are adapted to be screwed together.

8. A joint prosthesis according to claim 7, wherein the pressure piece comprises a pressure disc with a passage opening for the collar piece.

9. A joint prosthesis according to claim 8, wherein the pressure disc is annular.

10. A joint prosthesis according to claim 8, wherein the pressure disc is C-shaped.

11. A joint prosthesis according to claim 8, wherein the pressure piece is a cap nut or is fixable by a cap nut.

12. A joint prosthesis according to claim 11, wherein the pressure disc is rotatable relative to the shaft piece about an axis through the passage opening.

13. A joint prosthesis according to claim 12, wherein the cap nut is adapted to be connected to the shaft piece by a bayonet fastener.

14. A joint prosthesis according to claim 11, wherein the pressure piece is non-rotatable relative to the shaft piece with respect to an axis through the passage opening.

15. A joint prosthesis according to claim 8, wherein the pressure disc is adapted to be connected to the shaft piece by resilient clamping means.

16. A joint prosthesis according to claim 8, wherein the pressure disc is fixed on the shaft piece to be pivotable about an axis transversely of the collar axis.

17. A joint prosthesis according to claim 8, wherein the pressure disc is adapted to be clamped fast on the shaft piece by a clamping connection.

18. A joint prosthesis according to claim 2, wherein the edge is situated transversely of a direction of rotation of the collar piece about its collar axis.

19. A joint prosthesis according to claim 18, wherein at least one linear contact exists between the joint head and the pressure piece.

20. A joint prosthesis according to claim 1, wherein the pressure piece comprises a pressure disc with a passage opening for the collar piece.

21. A joint prosthesis according to claim 20, wherein the pressure disk is rotatable relatively to the shaft piece about an axis through the passage opening.

22. A joint prosthesis according to claim 20, wherein the pressure piece is non-rotatable relative to the shaft piece with respect to an axis through the passage opening.

23. A joint prosthesis according to claim 12, wherein the pressure disc is fixed on the shaft piece to be pivotable about an axis transversely of the collar axis.

* * * * *